United States Patent
Fretigny et al.

(10) Patent No.: US 6,349,591 B1
(45) Date of Patent: Feb. 26, 2002

(54) DEVICE AND METHOD FOR CONTROLLING THE INTERACTION OF A TIP AND A SAMPLE, NOTABLY FOR ATOMIC FORCE MICROSCOPY AND NANO-INDENTATION

(75) Inventors: Christian Fretigny, Paris; Denis Michel, Chatenay-Malabry, both of (FR); Benjamin Brocart, Montreal (CA); Charlotte Basire, Fontaine le Bourg (FR)

(73) Assignee: Universite Pierre & Marie Curie, Paris (FR)

( * ) Notice: Subject to any disclaimer, the term of this patent is extended or adjusted under 35 U.S.C. 154(b) by 0 days.

(21) Appl. No.: 09/482,005

(22) Filed: Jan. 13, 2000

(51) Int. Cl.$^7$ .............................. G07B 11/30; G07N 3/46
(52) U.S. Cl. ......................................................... 73/105
(58) Field of Search ............................. 73/105; 250/306, 250/307

(56) References Cited

U.S. PATENT DOCUMENTS

| | | | | |
|---|---|---|---|---|
| 5,210,425 A | * | 5/1993 | Delawski et al. | 250/307 |
| 5,553,487 A | * | 9/1996 | Elings et al. | 73/105 |
| 5,670,712 A | * | 9/1997 | Cleveland et al. | 73/105 |
| 5,804,708 A | * | 9/1998 | Yamanaka et al. | 73/105 |
| 5,866,807 A | * | 2/1999 | Elings et al. | 73/105 |
| 5,874,668 A | * | 2/1999 | Xu et al. | 73/105 |
| 5,880,360 A | * | 3/1999 | Hu et al. | 73/105 |
| 5,900,728 A | * | 5/1999 | Moser et al. | 250/306 |
| 6,185,991 B1 | * | 2/2001 | Hong et al. | 73/105 |

OTHER PUBLICATIONS

Slaughterbeck et al., J. Vac. Sci. Technol. A 14(3), May/Jun. 1996.*
Campbell, S. D. et al. "Nanometer–Scale Probing of Potential–Dependent Electrostatic Forces, Adhesion, and INterfacial Friction at the Electrode/Electrolyte Interface", Langmuir 1999, vol. 15, pp. 891–899.*

* cited by examiner

Primary Examiner—Hezron Williams
Assistant Examiner—Michael Cygan
(74) Attorney, Agent, or Firm—Arent Fox Kintner Plotkin & Kahn, PLLC

(57) ABSTRACT

A device for controlling the interaction of a tip and a sample includes a deformable element carrying the tip and means for positioning the tip with respect to the sample. The device also includes at lest two electrodes for creating an electrical field that exerts a force. The deformable element is preferably elastically deformable and includes advantageously a cantilever. According to a method for controlling the interaction of a tip and a sample, the tip carried by a deformable element is positioned with respect to the sample and the interaction of the tip and the sample is controlled by creating an electric field using a voltage between at least two electrodes. This electrical field exerts a force on the tip. Applications are to atomic force microscopy (AFM) and to nano-indentation measurements.

2 Claims, 5 Drawing Sheets

DEVICE AND METHOD FOR CONTROLLING THE INTERACTION OF A TIP AND A SAMPLE, NOTABLY FOR ATOMIC FORCE MICROSCOPY AND NANO-INDENTATION

BACKGROUND OF THE INVENTION

1. Field of the Invention

This invention relates to a device and a method for controlling the interaction between a tip and a sample, whereas the tip is carried by a deformable element and placed in relation to the sample by positioning means. The invention more particularly relates to local probe techniques, notably local probe microscopy such as for instance atomic force microscopy (AFM) or nano-indentation measurements.

2. Description of the State of the Technique

Atomic force microscopy is based upon the detection of interacting forces between a tip fixed at the extremity of a leaf spring called cantilever and the surface of the sample. The extremity of the tip is small and close to the surface. AFM microscopy uses tip-surface interaction forces for imaging, for measuring forces (adherence, friction, . . . ) and/or for acting on the surface.

Numerous AFM operating modes use deflection of the cantilever as a means for applying and/or measuring a force. This raises numerous difficulties when it is sought to obtain high force dynamics, to work in a liquid medium or to collect information of various natures with the same device (same zones analysed in the same experiment with the same probe). Moreover, certain mechanical measurements are difficult to interpret using the extant systems, owing to coupling phenomena between the force applied and the measurement obtained. Besides, the known systems generally do not keep the resonance qualities of the cantilever in liquid medium and do not allow for instance to carry out dynamic surveys of the double-layer phenomena or to measure the load properties of the samples.

As regards the measurement of mechanical properties (nano-indentation, scratch tests, force modulation, . . . ), the experimental arrangements involve offsets of the tip on the surface when applying a force, which makes the analysis of the results even more complicated. Moreover, using high stiffness values for the cantilever proves necessary in order to apply great forces, which is detrimental to a good detection sensitivity of the device.

In order to remedy the above shortcomings, several techniques have been suggested. Thus, one of them enables to excite the vibrations of the cantilever in a liquid environment by using a global vibration of a cell for liquids supporting the cantilever. This solution is however limited to low stiffness cantilevers and causes degradation of the resonance qualities of the cantilever.

Another solution employed in a liquid medium consists in causing the cantilever to oscillate using a magnetic field. This implementation however requires to achieve a cantilever possessing magnetic properties and to excite this cantilever magnetically. This implementation thereby calls for the use of specific cantilevers, rendered for instance magnetic by metal deposit. Further, the resonance qualities of the cantilever are also degraded.

A solution to the lateral displacement problems of the tip on the surface consists in applying an opposite lateral displacement corresponding to the vertical displacement. Besides the fact that this solution is barely approached, it does not solve the problem of the force dynamics.

The use of magnetic or conductive cantilevers subject to magnetic or electrostatic forces has also been suggested for measuring mechanical properties. These solutions imply however the realisation of specific cantilevers.

SUMMARY OF THE INVENTION

This invention relates to a device for controlling the interaction of a tip and a sample enabling to solve the above problems associated with atomic force microscopy, thus making possible to obtain high force dynamics, working in a liquid medium, including for the survey of surface loads and dynamics of the species in solution and gathering information of various natures with the same device.

The device of the invention may authorise the implementation of known AFM-operating modes in new or better experimental conditions, and enable moreover the carrying out of new surveys, notably analyses concerning the migration kinetics of the ions or the distribution of loads in the vicinity of a surface.

The device of the invention may be simple to use and economical and can be achieved without any particular difficulty out of a conventional atomic force microscope.

It may be used to perform elasticity measurements or to excite an intermittent contact mode as well as to negate the electrostatic load effect or to etch. Besides, a single device according to the invention may in particular enable to record images in intermittent mode, friction and a contact topography and to perform nano-indentation measurements.

The invention applies more generally to a device for controlling the interaction of a tip carried by a deformable element and positioned by positioning means against a sample.

This invention is also relative to a process for controlling the interaction of a tip and a sample, with the advantages mentioned above.

The device and the process according to the invention find applications notably in atomic force microscopy, especially for the survey of double-layer dynamic phenomena or of loads at the tip-sample interface in liquid medium, and in nano-indentation measurements.

More generally, the invention applies to local probes, such as in particular AFM or scanning tunnel microscopy (STM) devices. It is also usable for etching.

To this effect, the invention relates to a method for controlling the interaction of a tip and of a sample, comprising a deformable element carrying the tip and means for positioning this tip with respect to the sample. The device also comprises at least two electrodes, intended for creating an electric field capable of exerting a load on the tip.

The deformable element is preferably elastically deformable. In a preferred embodiment, it thus includes a cantilever, in particular in an AFM microscope. According to another advantageous embodiment, this elastically deformable element is a spiral spring.

According to a distinct embodiment, the deformable element is not elastically deformable, but comprises for example a ball joint and an articulated arm.

In local probe techniques, the tip is an element on which the interactions with the sample are concentrated. This element can be passive (enabling to measure interactions) or active (acting on the sample). Moreover, various embodiments of the device, and in particular of the tip, correspond to interactions of very different natures, such as notably mechanical interactions, in contact with or away from the surface, magnetic, electrostatic, optical and/or thermal interactions.

Preferably, the tip is dielectric, whereas the application of the electric field polarises this tip. In other embodiments, the tip is conductive or semi-conductive.

The differential voltage produced between both electrodes or more numerous electrodes, generates the electric field that produces an appropriate force on the tip.

Thus, it is acted directly on the tip instead of acting on the elastically deformable element (such as the AFM cantilever). More accurately, the forces created are generally distributed over the whole elastically deformable element, but essentially located on the tip (tip effect). This realisation, consequently, will notably decouple the applied load and the mechanical properties of the elastically deformable element.

The load applied to the tip using the electrodes has a static or dynamic effect according to whether the tip is subject to an opposite interaction force exerted by the sample or not. Thus, for example, the deformable element is almost not deformed in case of tip-sample contact in continuous mode and undergoes periodic deformations in resonance mode.

Among the embodiments of the device, various modes can be distinguished from a dynamic viewpoint, according to the time-related variations of the voltage applied between the electrodes:

the vibrating or oscillating mode, for which this voltage is periodic, for example sine wave or strobes, and has no quasi-static effect on the tip-sample interaction, the transitory mode, for which this voltage undergoes one or several discontinuities (sudden variations), and the continuous mode, for which this voltage has a quasi-static effect on the tip-sample interaction (the voltage can be for example constant or periodic); the voltage and the force are then said continuous.

The oscillating mode can itself be implemented or not in resonance mode, by exciting a resonance frequency of the deformable element. This resonance mode is particularly advantageous in a liquid medium.

The used frequency is preferably above a critical threshold of ion surface migration.

As regards the tip-sample interactions, contact-operating modes should be distinguished from contactless operating modes. The latter modes can be based in particular on Van der Waals, magnetic, electrostatic and/or double-layer interaction forces.

Interaction is advantageously exerted constantly (for example with permanent contact) or periodically (for example intermittent contact).

The means for positioning the tip with respect to the sample are provided in order to displace the sample (for example using a piezo-electrical tube) an/or the tip.

The possibility of using a dielectric tip with an elastically deformable element of any stiffness for all sorts of applications (excitation in a liquid medium, nano-indentation measurements, force modulation at the contact points, intermittent contact, . . . ) ensures simple use and economical realisation. In particular, it is not necessary to use for experiments in a liquid medium an acoustic or magnetic excitation device or for mechanical measurements a strongly doped or magnetic conductive or semi-conductive tip, which enhances simplicity and lowers the production costs.

Moreover, in nano-indentation, applying the force with contact induces only very few lateral displacements of the tip on the surface of the sample. Couplings with friction are thus eliminated and wear and etching surveys can be implemented with low stiffness cantilevers.

The possibility to use low stiffness cantilevers also enables to perform nano-indentation experiments in parallel with topography, friction or adherence measurements, using cantilevers foreseen for such measurements. Advantageously, it is thus resorted to a deformable element of which stiffness ranges from $10^{-2}$ to 0.1 N/m.

In a liquid medium, electrostatic excitation of the tip enables to keep resonance quality leading to pertinent and quantitative interpretation of the results obtained, and notably to study the double-layer dynamic phenomena at the tip-surface of the sample interface or to study the surface loads in the medium. Moreover, no specific treatment of the tip nor a cell for liquids is necessary.

In intermittent contact mode, using a low stiffness cantilever enables to perform different measurements at the same location of the sample, during a same experiment and with a same tip geometry. In particular, the intermittent contact may complete other contact analysis modes.

Another advantage of the device of the invention is the possibility to be integrated in microscopes available on the market, in order to improve the performances of the modes available and/or to add functionalities to those existing, economically.

The tip is preferably arranged between both electrodes. Thus, in a first preferred embodiment, the device comprises a sample-holder constituting a first of the electrodes and a conductive element provided in the vicinity of a support of the deformable element constituting a second of the electrodes. Advantageously, this second electrode is foreseen to be earthed. In a preferred form of this embodiment, the sample-holder is polarised with respect to the whole head of an atomic force microscope. In another preferred form, it is polarised with respect to an electrode located close to the tip. Moreover, the conductive element making up the second electrode is advantageously a long element carried by the support of the deformable element.

In a second embodiment, the device comprises a sample-holder making up a first of the electrodes which is foreseen to be earthed and a conductive element, preferably consisting of a rod or a wire, carried by the sample-holder and making up a second of the electrodes.

In another embodiment, the device comprises simultaneously an earth electrode and two other electrodes, which enables to generate attractive and repulsive forces at the same time.

The invention also relates to a method for controlling the interaction of a tip and a sample, in which the tip carried by a deformable element is positioned with respect to the sample and the interaction between the tip and the sample is controlled. To apply the tip against the sample, an electrical field is created using a voltage between at least two electrodes, whereas this electrical field exerts a load on the tip.

Preferably, the tip exerting on the sample a normal load and a friction force and the deformable element having a stiffness, a law giving the normal force in relation to the voltage between the electrodes is established beforehand, as follows:

the tip is applied against the sample using exclusively a deformation of the deformable element, the variation of the friction force is measured in relation to this deformation and the variation of the friction force in relation to the normal force is deducted therefrom using the stiffness of the deformable element, the tip is applied against the sample using exclusively the voltage between the electrodes and the variation of the friction force in relation to this voltage is measured, and the law giving the normal force in relation to the voltage between the electrodes is established using the variations of the friction force.

This optional calibration technique solves the problems associated with the measurement of the normal force. Indeed, the force applied not being obtained by deflection, it is not possible to read simply the deflection of a cantilever or any other deformation of the deformable element to measure the applied force. Quadratic dependency of the normal force is checked in relation to the voltage applied.

According to a first application mode of the voltage (oscillating mode), alternate voltage is applied between the electrodes, in order to cause the deformable element to vibrate. The deformable element having at least one resonance frequency, the deformable element is advantageously excited at these resonance frequencies or at half these frequencies (resonance mode). It is particularly interesting to use the oscillating mode in providing interaction between the tip and the sample in liquid medium (in resonance mode or not). More precisely, the tip and the sample having an interface in a liquid medium, double-layer dynamic phenomena at this interface and/or the loads in the vicinity of this interface are advantageously studied.

In a second application mode of the voltage (continuous mode), a continuous voltage is applied between the electrodes in order to exert a continuous force on the tip.

According to a third application mode of the voltage (transitory mode), a voltage discontinuity is applied between the electrodes, in order to produce a force discontinuity on the tip and thus to generate a transitory response of the interaction between the tip and the sample.

In a particular embodiment of tip-sample interaction, the tip is kept in contact with the sample.

This contact mode is advantageously combined with
  the application of a continuous voltage,
  or the application of an alternate voltage between the electrodes.

It is particularly interesting to implement this contact mode while performing nano-indentation measurements.

On FIGS. 1 to 3 and 9, the scales of magnitude have not been respected for visibility purposes. The values given in the description enable to complete the information of these figures.

Figure 1:
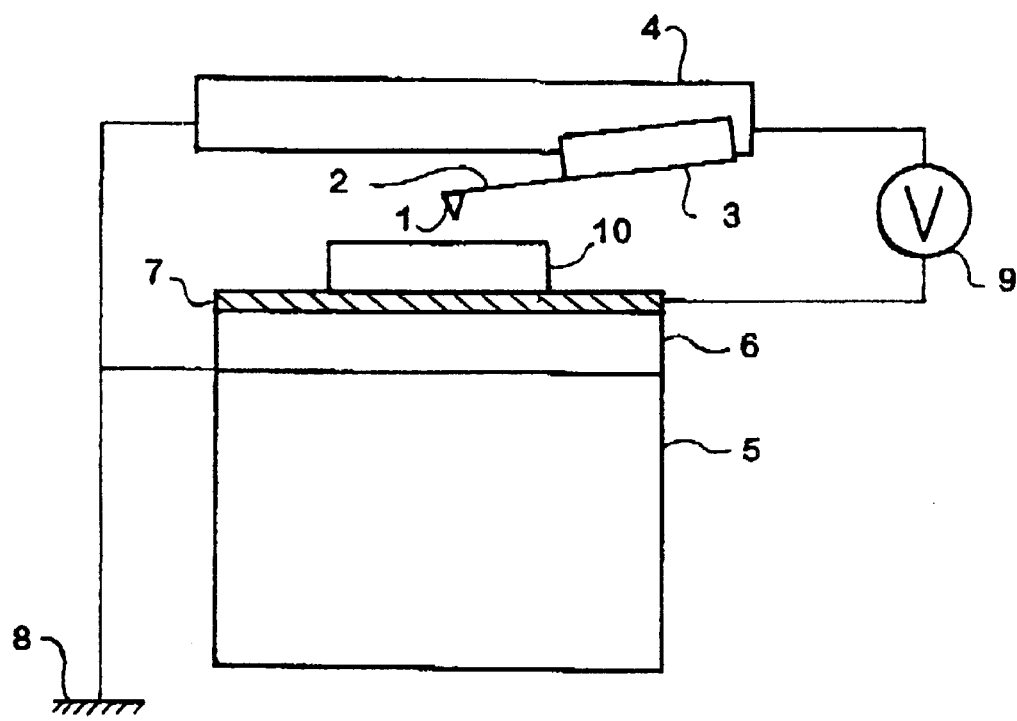
FIG. 1 is a principle diagram representing a first embodiment of a device for controlling the interaction of a tip and a sample according to the invention.
Figure 2:
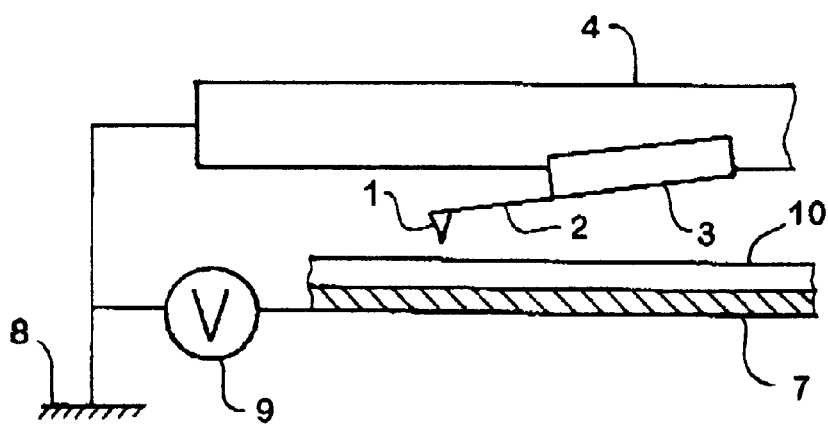
FIG. 2 is an enlarged representation of a portion of the device on FIG. 1.
Figure 3:
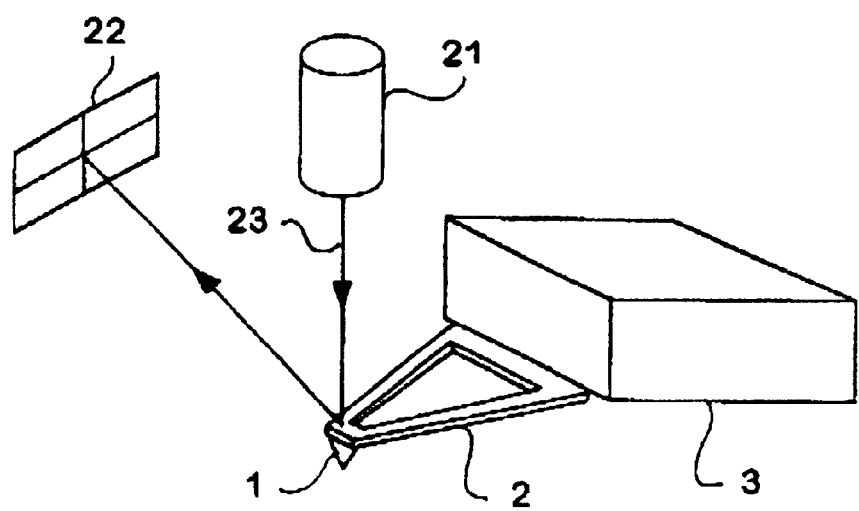
FIG. 3 is a principle diagram illustrating the detection system associated with the device of FIGS. 1 and 2.
Figure 9:
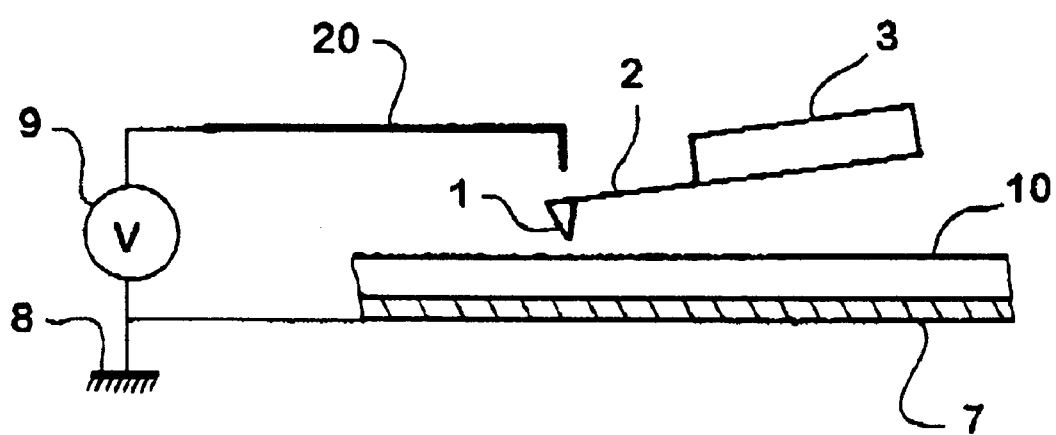
FIG. 9 is a principle diagram showing a significant portion of a second embodiment of a device for controlling the interaction of a tip and a sample according to the invention.

Moreover, on FIG. 9, elements identical or similar to those of FIGS. 1 to 3 are designated by the same references.

DETAILED DESCRIPTION OF THE PREFERRED EMBODIMENTS

An atomic force microscope (FIGS. 1 and 2) comprises a tube 5 made of piezo-electric ceramic, on which is placed a sample 10 to study. The deformation of the tube 5 under the effect of electric voltages between electrodes fixed to these walls causes a displacement of the sample 10, whereas the amplitude of the displacements may reach some hundred micrometers in the plane of the sample 10.

The sample 10, with for instance a 1-cm diameter, can be insulating or conductive.

The device also comprises a cantilever 2 carried by a substrate 3 and at the extremity of which is attached a tip 1. The cantilever 2 is a leaf spring, for example triangular (FIG. 3). According to a variation, the cantilever is rectangular. The size of the cantilever 2 is conventionally of a few hundred microns (for instance ranging between 100 and 500 microns) and the height of the tip 1 a few microns (for example between 1 and 20 microns). The cantilever 2 shows for instance a 10°-tilt with respect to the horizontal.

In the disclosed embodiment, the cantilever 2 and the tip 1 are made of a dielectric material. For exemplification purposes, the cantilever is made of silicon or of silicon nitride.

The device also comprises a detection system comprising a transmitter 21 for a laser beam 23, intended for being focused on the extremity of the cantilever 2 (FIG. 3), then reflected onto a mirror. A photodetector 22, for example consisting of a four-dial diode, is provided for receiving the beam sent back and for delivering electric voltages proportional to the lit surfaces.

The ceramic tube 5 is topped with an insulating layer 6, on which is applied a metal plate 7 serving as an electrode. Moreover, the upper surface of the tube 5 is linked to the earth 8.

The substrate 3 carries as for it, a conductive part 4 topping notably the cantilever 2 and the plate 7 carrying the sample 10, linked to the earth 8. This part 4 thus serves as an earthed electrode. In embodiment variations, it is replaced with any other element that may fulfil the same function. The substrate 3, comprising metal parts, is thus also earthed.

A voltage generator 9, direct or alternate voltage, links the part 4 to the plate 7, in order to apply a determined voltage to the electrode made of the plate 7.

In operation, a voltage is applied to the plate 7 using the generator 9, this voltage producing close to the tip 1 an electric field causing the polarisation of the cantilever 2 and the tip 1 and the production of a force that is mainly focused on the tip 1. This force is translated by a deflection of the cantilever 2 if the tip 1 is away from the surface of the sample 10 or by a reaction force in contact with this surface. More precisely, when the tip 1 and the surface of the sample 10 are close, they interact. The photodiodes of the photodetector 22 thus deliver electric voltages, of which differences are linked to deflection and torsion movements of the extremity of the cantilever 2.

In another embodiment (FIG. 9), the metal plate 7 is connected to the earth 8, in order to make up one of the electrodes and, instead of the part 4, the other electrode consists of a conductive element 20 formed of a rod placed above the cantilever 2. In an alternative embodiment, the conductive element is formed of a wire.

For a given surface of a sample, calibration can be performed with contact, before carrying out the measurements. This calibration enables to solve the difficulties associated with forecasting the normal force applied in relation to the voltage, since the geometry of the system is complex and it is not easy to calculate the distribution of the created field. It is proceeded as follows. First of all, the normal stiffness of the cantilever 2 is determined, at least approximately. Then normal forces are applied to the surface of the sample 10, by deflection and with zero polarisation voltage, while controlling the deflections using the deflection system comprising the transmitter 21 and the photodetector 22. Then the friction law in relation to the normal force applied is measured.

In another stage, no normal force is applied by deflection, but forces are exerted using the polarisation voltage and the friction law is measured in relation to this voltage.

The law giving the normal force in relation to the applied voltage is thus extracted from both these categories of measurement. The quadratic dependency of this law can be checked. Simple implementation of this voltage then enables to obtain accurate results.

It is interesting to notice that with a sensitive cantilever employed usually for experiments in contact mode, it is thus possible to obtain forces at least ten times greater than those that are typically obtained by deflection of the cantilever with voltages of a few ten volts. Moreover, the corresponding deflection is quasi non-existing. Besides, controlling the actions exerted on the tip 1 can be extremely accurate, in spite of what the complexity of the prevailing electrical phenomena might lead to think.

The applications of this technique include the use of a direct voltage enabling to apply a constant force on the sample or an alternate force to cause the cantilever 2 to vibrate. The examples given above have been obtained with the first embodiment of the device (FIGS. 1 to 3).

EXAMPLE 1

This example relates to resonant mode imaging in liquid medium by intermittent contact. It is proceeded as indicated above, the part 4 being used to keep the device in the water. Advantageously, the sample 10 being insulating, the conductive part 4 is placed in the liquid and the plate 7 is not in contact with the liquid. This arrangement enables to avoid spurious chemical reactions. The cantilever 2 having a 136-kHz resonance frequency in water (and approximately 300 kHz in the air), a sine wave of approx. 20 volts at this frequency is applied using the generator 9.

Figure 4:
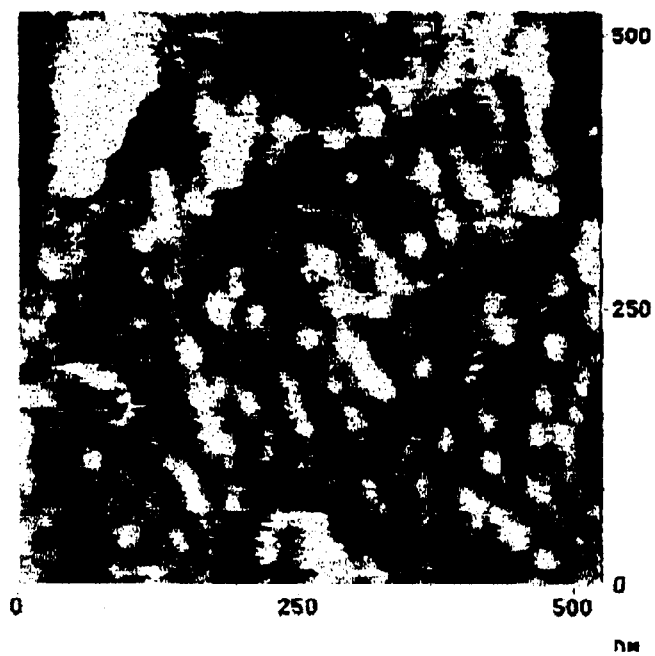
FIG. 4 is a photo showing a polystyrene-polyisoprene-polystyrene (PS-PI-PS) surface, observed in water using a device such as that of FIGS. 1 to 3 in resonance mode imaging.

This technique is used to study a sample 10 with a surface formed of a copolymer film of the polystyrene-polyisoprene-polystyrene type. A good resolution image is thus obtained (FIG. 4).

Figure 5:
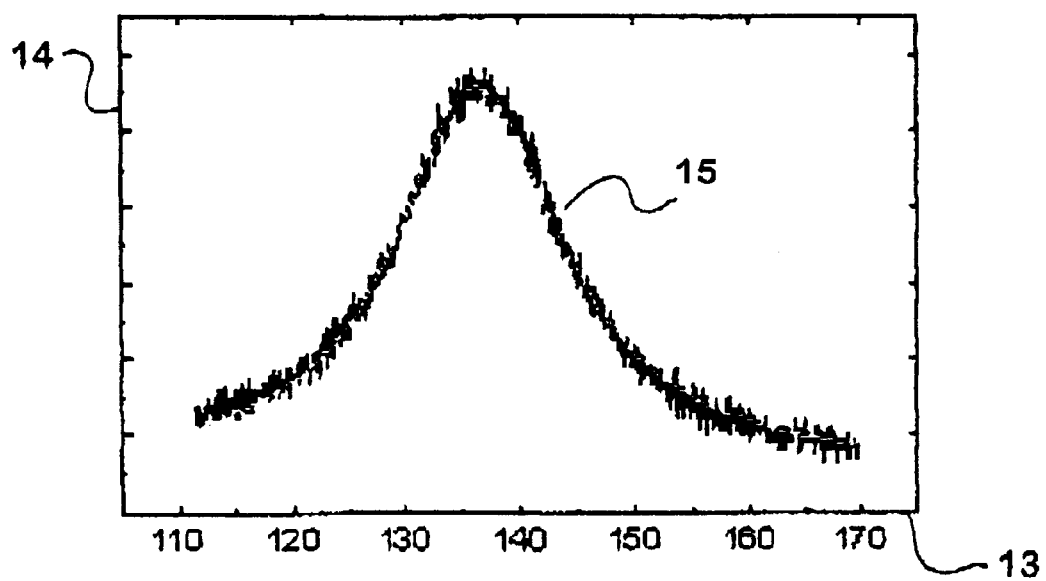
FIG. 5 represents a resonance spectrum of the cantilever of the device of FIGS. 1 to 3, obtained in the same conditions as for FIG. 4.

Moreover, resonance spectral curves are provided, such as the curve 15 (FIG. 5) giving the response intensity (axis 14) in relation to the frequency (axis 13, in kHz). It can be observed that the form of the spectrum obtained is very pure, much more than for spectral curves measured with either a classical mechanical or magnetic excitation. The dynamic properties of the cantilever 2 are therefore very well preserved.

EXAMPLE 2

Figure 6:
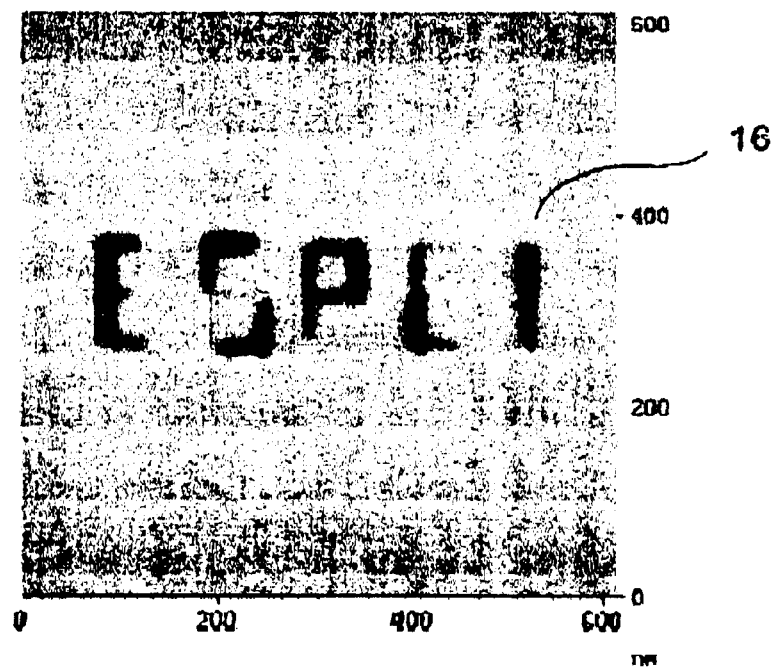
FIG. 6 is a photo representing a mica surface that has been wear-etched under a 100-volt continuous polarisation using a device such as that of FIGS. 1 to 3.

This example relates to the application of a static force for etching. The cantilever 2 has a rated stiffness of 0.6 N/m and a direct voltage equal to 100 V is applied using the generator 9. The surface of the etched sample 10 is a mica surface. While implementing the method described above, in a few passages of the tip 1, lines 16 are etched (FIG. 6) with a width of some twenty nanometers and 1-nm depth, corresponding to the thickness of a crystallographic sheet.

It can be noted that a great static force can be applied with a cantilever with relatively low stiffness and therefore with good sensitivity, without changing the point of application on the surface (no or little deflection).

It can be also checked that on the electrostatically loaded surfaces, as is often the case with polymers, for example, this device enables to negate the effect of the surface loads while creating an opposite field.

EXAMPLE 3

Figure 7:
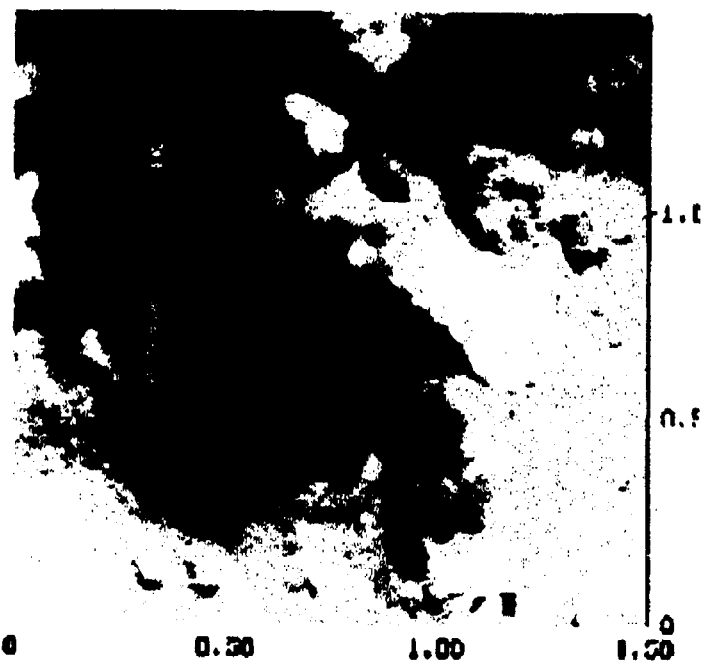
FIG. 7 is a photo illustrating the frictions obtained on a rubber alloy using a device such as that of FIGS. 1 to 3.
Figure 8:
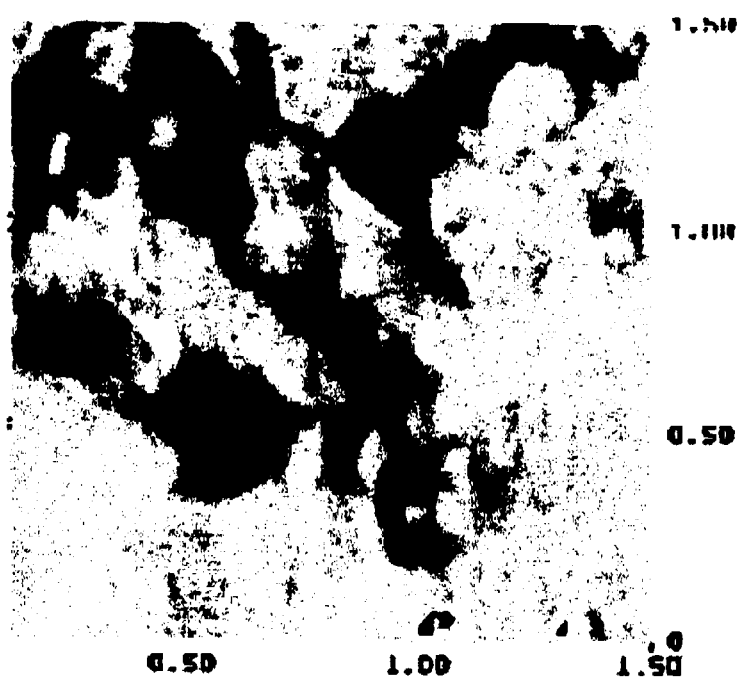
FIG. 8 is a photo showing the elasticity properties of the surface of a rubber alloy represented on FIG. 7, obtained using a device such as that of FIGS. 1 to 3 by an excitation of the resonance of the cantilever, simultaneously to the friction results represented on FIG. 7.

In this other example, the resonance of the cantilever 2 is excited while measuring offsets of the resonance frequency when the tip 1 is in contact with a mechanically heterogeneous material consisting of a rubber alloy. The image obtained reveals heterogeneities (FIG. 8: elasticity). The contrast observed is indeed decoupled from topography or frictions (FIG. 7: frictions), that are preferably measured simultaneously.

What is claimed is:

1. A control device for controlling interaction of a tip and a sample, comprising:

a deformable element carrying a tip, means for positioning the tip with respect to the sample, the device also comprising at least two electrodes, distinct from the tip, that create an electrical field for exerting a force on the tip; wherein the control device is housed in an atomic force microscope; and wherein the device comprises a sample-holder making up a first of the electrodes and a conductive element comprising a rod or a wire, carried by the sample-holder and making up a second of the at least two electrodes, one of said electrodes being earthed.

2. A control device for controlling interaction of a tip and a sample, comprising:

a deformable element carrying a tip, means for positioning the tip with respect to the sample, the device also comprising at least two electrodes, distinct from the tip, that create an electrical field for exerting a force on the tip; and wherein the control device is housed in a local probe.

* * * * *